(12) United States Patent
Quinn et al.

(10) Patent No.: US 6,448,347 B1
(45) Date of Patent: Sep. 10, 2002

(54) CONTINUOUS PRODUCTION OF 2-ACRYLAMIDO-2-METHYLPROPANE-SULFONIC ACID IN A SMALL REACTOR INTEGRATED WITH ACRYLIC POLYMER FIBER PRODUCTION

(75) Inventors: Robert E. Quinn, Cleveland; William Michael Burk, Chardon, both of OH (US)

(73) Assignee: The Lubrizol Corporation, Wickliffe, OH (US)

(*) Notice: Subject to any disclaimer, the term of this patent is extended or adjusted under 35 U.S.C. 154(b) by 0 days.

(21) Appl. No.: 09/426,799

(22) Filed: Oct. 22, 1999

Related U.S. Application Data

(60) Provisional application No. 60/111,827, filed on Dec. 11, 1998.

(51) Int. Cl.[7] .............................. C08J 2/00; C08G 85/00
(52) U.S. Cl. ................... 526/67; 526/303.1; 526/307.2; 526/348.7; 562/41; 562/105
(58) Field of Search ................ 562/41, 105; 526/303.1, 526/307.2, 67, 348.7

(56) References Cited

U.S. PATENT DOCUMENTS

| | | | |
|---|---|---|---|
| 2,983,712 A | 5/1961 | Wilkinson | 260/79.3 |
| 3,506,707 A | 4/1970 | Miller | 260/513 |
| 3,544,597 A | 12/1970 | Killam | 260/332.1 |
| 3,547,899 A | 12/1970 | Arlt et al. | 260/79.3 |
| 4,034,001 A * | 7/1977 | Miller et al. | 260/513 |
| 4,226,824 A | 10/1980 | Cazzaro et al. | 264/182 |
| 4,255,532 A | 3/1981 | Daftary | 525/59 |
| 4,309,475 A | 1/1982 | Hoffman | 428/370 |
| 4,324,095 A | 4/1982 | Lulay et al. | 57/327 |
| 4,524,193 A | 6/1985 | Yamazaki et al. | 526/79 |
| 4,650,614 A | 3/1987 | Jevne et al. | 260/513 |
| 4,701,823 A * | 10/1987 | Itoh et al. | 562/41 |

FOREIGN PATENT DOCUMENTS

| | | |
|---|---|---|
| CA | 704778 | 3/1965 |
| GB | 1090779 | 4/2000 |

* cited by examiner

*Primary Examiner*—David W. Wu
*Assistant Examiner*—Tatyana Zalukaeva
(74) *Attorney, Agent, or Firm*—David M. Shold; Michael F. Esposito

(57) ABSTRACT

Amidoalkanesulfonic acids are prepared by reacting a molar excess of an unsaturated nitrile, a source of $SO_3$, and an olefin, in a substantially non-aqueous medium, and transferring the crude reaction product containing amidoalkanesulfonic acid, without substantial purification steps, into an apparatus for incorporation of the amidoalkanesulfonic acid into a copolymer.

22 Claims, 1 Drawing Sheet

CONTINUOUS PRODUCTION OF 2-ACRYLAMIDO-2-METHYLPROPANE-SULFONIC ACID IN A SMALL REACTOR INTEGRATED WITH ACRYLIC POLYMER FIBER PRODUCTION

This application claims priority from U.S. Provisional Application No. 60/111,827 filed on Dec. 11, 1998.

BACKGROUND OF THE INVENTION

The present invention relates to continuous production of acrylamidoalkanesulfonic acid in a small reactor in connection with acrylic fiber production.

Acrylamidoalkanesulfonic acids are commercially important monomers, useful in the preparation of copolymers suitable for number of applications, including ion exchange resins, polymers useful for increasing the affinity of acrylonitrile copolymers for basic dyes, copolymers useful as resins and films, as well as in the preparation of flocculants, dispersants, adhesives, and thickeners. (The term "copolymer" as used herein includes terpolymers and other higher order copolymers.)

The preparation of such monomers is known. Manufacturing processes generally involve extensive isolation, purification, and recycling steps. U.S. Pat. No. 3,544,597, Killam, Dec. 1, 1970, discloses a process of preparing lower alkyl- and olefinic-amido-sulfonic acids. A nitrile, olefin and fuming sulfuric acid are sequentially mixed together at a temperature of between−30° and 45° C. The resulting sulfonated amides are insoluble in an excess of the nitrile employed as the sole solvent, the amides being obtained directly by filtration and in a high state of purity.

Acrylamidoalkane sulfonic acids can be used as dye sites in acrylic fibers. There are several processes for the polymerization of acrylonitrile or other acrylics for acrylic fiber production. U.S. Pat. No. 4,255,532, Daftary, Mar. 10, 1981, discloses an acrylic polymer composition for melt spinning. A combination of a major amount of acrylonitrile and a minor amount of another monomer copolymerizable with acrylonitrile when grafted onto polyvinyl alcohol provides an improved acrylonitrile polymer for preparing fiber by extruding a fusion melt of such polymer and water.

U.S. Pat. No. 2,893,712, Wilkinson, May 9, 1961, discloses polymers of acrylonitrile containing polymerizable sulfonated vinyl monomers. The monomers may be represented by the formula $CH_2=C(R)CONHR'(SO_3X)_n$. Polymerization of the monomers and copolymerization of these monomers with hydrophobic monomer such as acrylonitrile may be carried out using the crude aqueous reaction product or by using the purified materials. In an example, sodium 2-methacrylamidoethanesulfonate is prepared and the crude product filtered and dried. The crude product is copolymerized with acrylonitrile by a continuous procedure.

The present invention solves the problem of extensive purification and recycling of reactants in the manufacturing of amidoalkanesulfonic acids by integrating the process for the manufacture thereof with the manufacture of acrylic fibers.

SUMMARY OF THE INVENTION

The present invention provides a method for preparing and/or supplying an amidoalkanesulfonic acid feed stream suitable for incorporation into a polymer, comprising (a) combining under reactive conditions a molar excess of an unsaturated nitrile, a source of $SO_3$ and of the elements of water, and an olefin, in a substantially non-aqueous medium wherein the molar ratio of water to $SO_3$ is about 0.5 to about 1.5, thereby forming an amidoalkanesulfonic acid as a component of a crude reaction product; and (b) transferring the crude reaction product from (a), without substantial purification steps, into an apparatus for incorporation of the amidoalkanesulfonic acid into a copolymer.

The invention further provides a method for preparing a copolymer comprising amidoalkanesulfonic acid monomer units and unsaturated nitrile monomer units, comprising the steps of (a) transferring into a polymerization reactor the crude reaction product prepared by the above-described method and (b) polymerizing the resulting material Otherwise stated, the invention also provides a method for preparing a copolymer comprising amidoalkanesulfonic acid monomer units and unsaturated nitrile monomer units, comprising the steps of (a) transferring into a polymerization reactor (i) the crude reaction product prepared by the above-described and (ii) an unsaturated nitrile monomer in addition to any unsaturated nitrile monomer which may be present in (i); and (b) polymerizing the resulting mixture.

DETAILED DESCRIPTION OF THE INVENTION

Figure 1:
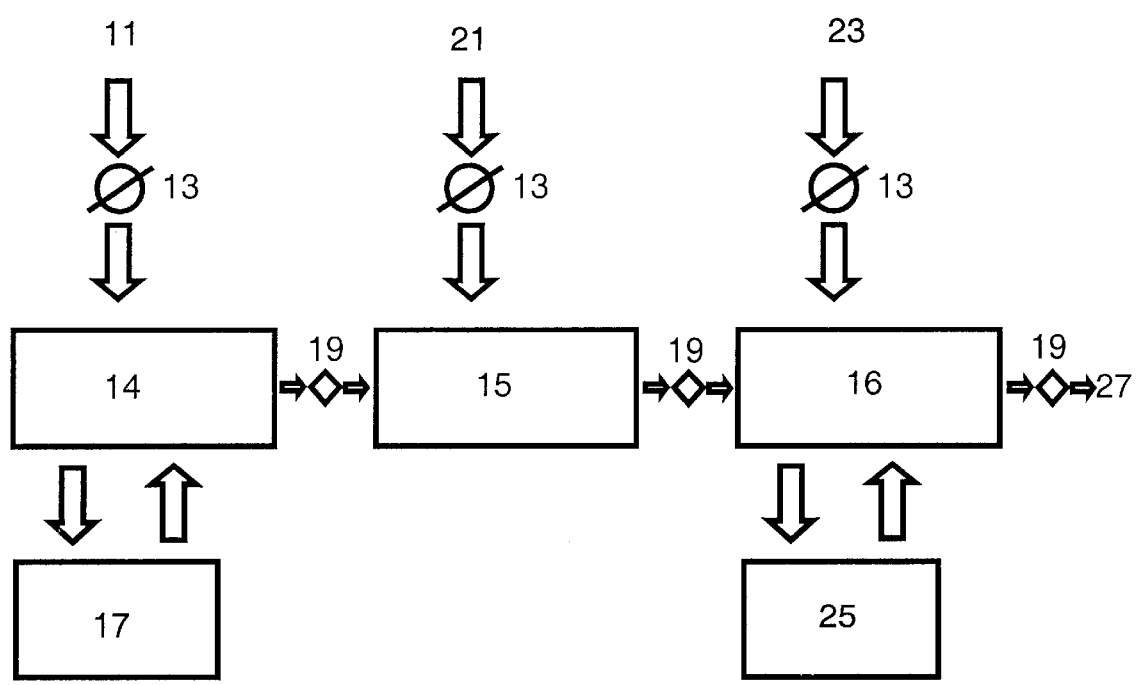
FIG. 1 shows in diagrammatic fashion the elements of a reactor suitable for preparing amidoalkanesulfonic acid.

Various preferred features and embodiments will be described below by way of non-limiting illustration.

Acrylamidoalkanesulfonic acids (hereinafter generically AAMSA) are materials represented by the formula

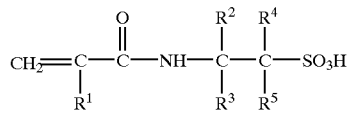

wherein, in the preferred embodiments, $R^1$ is hydrogen or a lower hydrocarbyl or alkyl radical and each of $R^2$, $R^3$, $R^4$, and $R^5$, is independently hydrogen or an alkyl or hydrocarbyl radical. $R^2$ can also be $—CH_2SO_3H$, providing a disulfonic acid, and mixtures of such materials can generally be found in the crude reaction product of the present invention when the olefin from which the product is derived is isobutylene. The term "lower" as used in this context designates radicals containing up to 7 carbon atoms. The term "acrylamidoalkanesulfonic acid" thus includes materials made from methacrylonitrile ($CH_2=CR^1CN$ where $R^1$ is methyl), methacrylonitrile, and the like, and not just acrylonitrile. Preferably the alkyl group $R^1$ has 6 or fewer carbon atoms, more preferably 3 or fewer carbon atoms. More preferably yet $R^1$ is methyl, and most preferably it is hydrogen.

Preferably each of $R^2$, $R^3$, $R^4$, and $R^5$ in the formula above is independently hydrogen or a lower alkyl radical, and such substituents are similarly defined for the precursor olefin $R^2R^3C=CR^4R^5$. In a preferred embodiment, $R^2$ and $R^3$ are each methyl, while $R^1$, $R^4$, and $R^5$ are each hydrogen. Such a material is 2-acrylamido-2-methylpropane sulfonic acid, represented by the formula

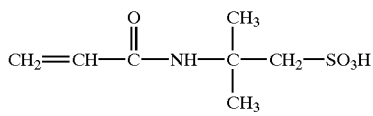

(The commercial grade material is believed to include a byproduct fraction containing two sulfonic acid groups as described above, that is, where $R^2$ is a —$CH_2SO_3H$ group; this and related materials are similarly considered to be a part of the present invention.) This material is commercially available from The Lubrizol Corporation as AMPS® monomer, or from Toa Gosei. Other useful materials of the class of AAMSA generally, include 2-acrylamidoethanesulfonic acid, 2-acrylamidopropanesulfonic acid, 2-methacrylamidopropanesulfonic acid, and 2-methacrylamido-2-methylpropanesulfonic acid. Such materials and methods for their preparation are disclosed, for instance, in U.S. Pat. No. 3,544,597.

As used herein, the term "hydrocarbyl substituent" or "hydrocarbyl group" is used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form a ring);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

AAMSA materials have in the past been typically prepared and isolated for use or sale as substantially pure compounds. In the application of the present invention, however, the crude product of the process described below is used without substantial purification steps, that is, without separation or isolation of the intermediate product or recycling of solvent, although neutralization or some concentration, dilution, or other incidental processing may occur. The result can be a significant savings and simplification of the process. This is possible because unreacted starting materials, such as excess acrylonitrile, and byproducts, such as the disulfonated material referred to above, t-butyl acrylamide, and isobutylene sulfonic acid, including both the mono- and di-sulfonic acids, e.g., 2-methyl-2-propene-1-sulfonic acid, are compatible with or even functional in the reaction mixture into which they are subsequently fed. In the present invention, AAMSA can be used as a dye site receptor in acrylic fiber and is incorporated as a comonomer during the polymerization of the acrylic monomers.

The AAMSA is prepared by the reaction of an unsaturated nitrile and an olefin in the presence of a source of $SO_3$ such as sulfuric acid or oleum (fuming sulfuric acid, i.e., sulfuric acid containing excess $SO_3$, typically 15, 20, or 30% excess). In a preferred case the unsaturated nitrile is acrylonitrile and the olefin is isobutylene, the product being AMPS® monomer. The present reaction is conducted in a substantially non-aqueous medium. That is, it is not conducted in a water solution or water slurry, in contrast to a process which might involve preparation of similar monomers by the reaction of an aminoalkanesulfonate with an acrylyl or methacrylyl chloride in a water medium, as disclosed generally in U.S. Pat. No. 2,983,712. Moreover, the water present in the reaction medium according to the present invention should be limited to certain specific amounts in order for the reaction to proceed properly. From a stoichiometric point of view, one mole of water is required to react along with each mole of $SO_3$, according to the equation $H_2C$=$CH$—$CN$ + $(CH_3)_2C$=$CH_2$ + $SO_3$ + $H_2O$ ⟶

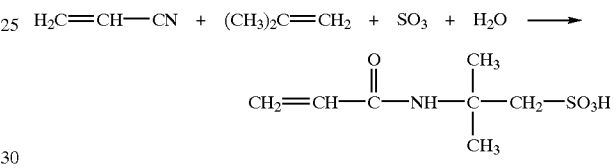

This mole of water can be supplied bound to the $SO_3$ in the form of $H_2SO_4$ or it can be supplied independently of the $SO_3$. Some of such water can be introduced along with the unsaturated nitrile (e.g., acrylonitrile) feed, since the nitrile is typically not entirely anhydrous. The total moles of water present, whether bound to the $SO_3$ or free, should be 0.5 to 1.5 times the number of moles of $SO_3$ (whether as $SO_3$ or as $H_2SO_4$) present in the mixture. Preferably the molar ratio is 0.6 to 1.2, and more preferably 0.7 to 1.1 or 1.05. Thus there is preferably at most only a small amount of excess water present, although there can be a stoichiometric excess of $SO_3$. In an otherwise absolutely anhydrous environment, $H_2SO_4$ would be the preferred source of $SO_3$, in which case the ratio of water:$SO_3$ would be 1:1. For ordinary purposes sufficient water will be present from one source or another, and it may be appropriate to speak merely of a required source of $SO_3$, the presence of water being implicit. Equivalently, one could speak of a required source of $H_2SO_4$ or the elements of $H_2SO_4$, or of a source of $SO_3$ and the elements of water.

The molar ratios of the raw materials are typically such that the ratio of oleum:isobutylene is 0.7 or 0.8 to 2.0, preferably 0.9 to 1.5, more preferably 0.95 or 1.0 to 1.1 or 1.2; the acrylonitrile:isobutylene ratio is 2 to 20, preferably 4 to 15, more preferably 5 or 6 to 12. This represents a molar excess of acrylonitrile, which can thus serve as a reaction medium as well as a reactant. However, the excess acrylonitrile also conveniently functions as a carrier for the crude product; and normally acrylonitrile is used for the preparation of acrylic polymer for fibers. Accordingly, the excess acrylonitrile will normally be fed into the fiber unit along with the AMPS® monomer. (At low acrylonitrile:isobutylene ratios, precautions should be taken to avoid uncontrolled reaction of sulfuric acid with acrylonittrile.)

In a preferred continuous process, 29.3 moles of acrylonitrile is chilled to −20° C. and combined with 2.0 moles of 20% oleum (based on total moles of sulfur in the oleum as either $H_2SO_4$ or $SO_3$). Upon mixture, heat of solution leads to an increase in temperature of about 10° C. The mixture is combined with 1.78 moles of isobutylene and allowed to return to room temperature. When the reaction is thus conducted in two substeps (i.e., (i) combining the unsaturated nitrile, the source of $SO_3$ and of the elements of water, and (ii) adding the olefin to the mixture of (i)) a preferred temperature for the first substep is −30 to 0° C. and a preferred temperature for the second substep is 20 to 70° C. A preferred overall temperature range is −20 to 40° C.

The foregoing conditions are preferred for the case in which the feed of acrylonitrile is of a comparatively large volume and/or is not entirely free from water (e.g., about 0.45 percent by weight). At relatively low volumes of dry acrylonitrile, however, concentrated sulfuric acid can be substituted for the 20% oleum and only minimal or even no cooling of the reactants would be required. Processing can be done at atmospheric pressure or other pressure as desired. Generally no added catalyst is required.

The reactor or reactor segments can be constructed of stainless steel or other suitable chemically resistant materials. The reactor sections can contain static mixers or plug flow reactors and are preferably of a sufficient length to assure adequate mixing and residence times to achieve a uniform product.

Upon exiting the reactor, the product stream can generally be fed directly into an acrylic fiber unit without further treatment. However, if the acid form of the AAMSA should be inappropriate for the particular polymerization process employed, the AAMSA can be neutralized to form a salt, especially a sodium salt, by well-known methods such as addition of NaOH and mixing. Additional processing steps can be employed, if desired; these include dilution of the product to a desired concentration; neutralization of the AAMSA; addition of different or additional solvents, such as dimethylformamide, which may be appropriate for certain polymerization operations; or adjustment of the pH. If pH adjustment is effected by addition of a solution or dispersion of a carbonate such as sodium carbonate, equipment may be provided to allow for degassing to remove the resulting carbon dioxide.

The flow rate of components through the reactor can be varied to suit the desired output. When the output is to be fed directly into an acrylic fiber unit, the flow rate will be determined based on the size of that unit and the desired AAMSA/fiber treatment ratio. For a typical fiber line, running a continuous process and producing 100 metric tons of fiber per day with a 1% treatment of AMPS® monomer, the unit will be adjusted to produce 1 metric ton of AMPS® monomer per day. The flow of reactants and products can be measured by conventional metering devices.

The process for preparing AAMSA monomer is preferably practiced in conjunction with an acrylic polymerization line which consumes acrylonitrile. The process could indeed be conducted as a stand-alone unit, but an economic burden encountered under such conditions is the handling and treatment of the excess acrylonitrile used in the manufacture. For each mole of acrylonitrile consumed, a relatively large number (up to about 14) moles would need to be recycled, as well as an additional several (e.g., 5) moles would be used in the purification of the crude grade AMPS® monomer. These difficulties are avoided when the process is integrated into an acrylic polymerization process. The crude AMPS® monomer stream can be fed into the polymerization unit, since indeed many of the typical byproducts and impurities can be approximately as effective as the AMPS® monomer itself in providing dye receptivity to acrylic fibers.

FIG. 1 shows in diagrammatic fashion the elements of a reactor suitable for preparing amidoalkanesulfonic acid. Acrylonitrile is fed into the system at 11 through a flow controller 13 and into a cooling unit 14. The contents of the cooling unit are maintained at reduced temperature by means of a chiller 17. The cooled material from the cooling unit is passed through a check valve 19 into a mixing unit 15, to which oleum is added at 21. The mixture is passed through another check valve into a reaction unit 16, at which point isobutylene is added at 23. The contents of the reaction unit are maintained at a desired or elevated temperature by means of a heater 25. After a suitable residence time, the product, comprising crude AMPS® monomer, passes from the reactor assembly at 27 into an acrylic polymerization reactor unit, not shown.

There are several processes for the polymerization of acrylonitrile or other acrylics for acrylic fiber production. Two such processes that are of particular interest in the present invention are the so-called SNIA (Societa Nazionale Industria Applicazionic Viscosa S.p.A.) process and the Cortaulds process. The SNIA process is described in U.S. Pat. 4,287,148, which discloses preparing fibers by wet spinning a polyblend obtained by mixing two binary copolymers. The first copolymer is from acrylonitrile and a sulfonated comonomer, and the second is from acrylonitrile and vinylidene chloride. The spinning dope is a polyblend solution in an organic solvent, mixed with water. The acrylonitrile-sulfonated comonomer polymer can be prepared by any of the known acrylonitrile copolymerization methods, viz., in aqueous emulsion or dispersion, in bulk, or in solution. Suitable conditions for this reaction include polymerization at 60 to 80° C. (disclosed: 67° C. for 11 hours) using a small amount of an AIBN catalyst and maleic acid stabilizer in dimethylformamide solvent.

The Cortaulds process is believed to involve polymerization of acrylonitrile with 2–10%, preferably 5–6% methacrylate and a smaller amount, e.g., about 1% itaconic acid as the sodium itaconate (which would normally be replaced by the AAMSA when the present invention is employed). In one variation of this solution polymerization process, the components are dissolved in a solution containing sodium thiocyanate and reacted using an azoisobutyronitrile catalyst. The components are initially mixed together for approximately 4 hours at 25° C. and pH approximately 5. Thereafter the mixture is reacted for 1.8 to 2 hours at 79–82° C. under 340 kPa (3.5 kg/cm$^2$) pressure. Unreacted monomer is recycled. Residual monomer is removed from the polymer under vacuum.

Other catalytic systems and temperatures for the polymerization can be employed, and suitable values for such variables will be apparent to those skilled in the art. Temperatures, for example, will typically be in the range of 40, 50, or 60° C. up to 80 or 70° C.

Polymers or fibers from such processes, particularly when the polymers contain an appropriate level of AAMSA comonomer, can be dyed by treatment, under conventional dying conditions, with well-known basic dyes, available from a variety of suppliers such as BASF.

It is known that some of the materials described above may interact under reaction conditions or in mixtures in ways which are not easy to predict or describe. Any products formed thereby, including products formed upon employing compositions described in connection with the present, invention in their intended use, and modifications thereof, are included within the scope of the present invention; the present invention encompasses the composition prepared by admixing the components described above.

EXAMPLES

Example 1

To a jacketed, stirred 90 mL glass laboratory reactor are fed, continuously, acrylonitrile at 15.6 g/min (containing 0.45% water), and 20% oleum (104.5% $H_2SO_4$) at 1.88 g/min. The mixture is stirred and cooled by circulating coolant at about −32° C. through the jacket. (The same coolant is also used to precool the acrylonitrile feed). The mixture of acrylonitrile and oleum exiting the first reactor (at −8° C.) is fed to a second jacketed, stirred 1200 mL glass reactor, to which is also fed isobutylene at 1.00 g/min through a sub surface tube. The temperature of the second reactor is controlled to about 37° C. by circulating water at 35° C. through its jacket. The residence time in the second reactor is approximately 60 minutes. The product exiting the second reactor is a slurry which will contain about 19.3 percent of 2-acrylamido-2-methylpropanesulfonic acid along with byproducts (principally 2-acrylamido-2-methylpropane-1,3-disulfonic acid) in acrylonitrile. The product is the output of the reactor, which is sent to a holding vessel or can be fed directly to a polymerization unit. The product can be used without purification or recycling of any components

Example 2

Example 1 is substantially repeated except that the flow of acrylonitrile is 10.0 g/min and the water content thereof is 0.15%; the oleum is replaced by 99.2% $H_2SO_4$, at a flow rate of 1.95 g/min. The product is a slurry which will contain about 27.2 percent 2-acrylamido-2-methylpropanesulfonic acid in acrylonitrile. Example 3.

Example 2 is repeated without pre-chilling the acrylonitrile, thereby conducting the synthesis at substantially room temperature. Example 4.

Example 1 is substantially repeated except that the flow of acrylonitrile is 15.0 g/min, the acrylonitrile contains 0.15% water, and the oleum is fed at 3.35 g/min. The product is a slurry which will contain about 26.7% 2-acrylamido-2-methylpropanesulfonic acid. Example 5.

To a jacketed 2 L glass reactor equipped with stirrer and nitrogen purge is charged 100 g of a solution of $FeSO_4$ (concentration, 5 mg/L) and sufficient 0.1N $H_2SO_4$ to provide a pH of 3.1. The mixture is heated with stirring to 50° C. Four mixtures are separately prepared: (a) 92 g acrylonitrile and 6.5 g methyl acrylate; (b) 100 g water and 0.54 g $Na_2S_2O_8$, (c) 100 g water and 1.08 g $Na_2S_2O_5$, and (d) 100 g of an aqueous solution of $FeSO_4$ (concentration, 20 mg/L) and 10.4 g of the crude product slurry of Example 1. The contents of each mixture (a) through (d) are added continuously to the reactor over a period of 20 minutes. Thereafter the reaction mixture is maintained at 50° C. for an additional 30 minutes, with stirring, during which time an additional 200 g water is added in order to maintain appropriate viscosity. The resulting mixture is filtered to isolate polymer, which is dried under vacuum for several hours.

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diligent which may be customarily present in the commercial material, unless otherwise indicated. It is to be understood that the upper and lower amount, range, and ratio limits set forth herein may be independently combined. As used herein, the expression "consisting essentially of" permits the inclusion of substances which do not materially affect the basic and novel characteristics of the composition under consideration.

What is claimed is:

1. A method for preparing an amidoalkanesulfonic acid feed stream suitable for incorporation into a polymer, comprising
    (a) combining under reactive conditions a molar excess of an unsaturated nitrile, a source of $SO_3$ and of the elements of water, and an olefin, in a substantially non-aqueous medium wherein the molar ratio of water to $SO_3$ is about 0.5 to about 1.5, thereby forming an amidoalkanesulfonic acid as a component of a crude reaction product which includes the substantially non-aqueous medium, unreacted starting materials, and byproducts; and
    (b) transferring the crude reaction product from (a), including the substantially non-aqueous medium, unreacted starting materials, and byproducts, as a feed stream without substantial purification steps, into an apparatus for incorporation of the amidoalkanesulfonic acid into a copolymer.

2. The method of claim 1 wherein the unsaturated nitrile is represented by the structure $CH_2=CR^1CN$ where $R^1$ is hydrogen or an alkyl group containing up to about 7 carbon atoms.

3. The method of claim 1 wherein the unsaturated nitrile is acrylonitrile, methacrylonitrile, or methacrylonitrile.

4. The method of claim 1 wherein the unsaturated nitrile is acrylonitrile.

5. The method of claim 1 wherein the source of $SO_3$ and of the elements of water is sulfuric acid or oleum.

6. The method of claim 1 wherein the olefin is represented by the structure $R^2R^3C=CR^4R^5$ in which each of $R^2$, $R^3$, $R^4$, and $R^5$ is independently hydrogen or an allyl radical containing up to about 7 carbon atoms.

7. The method of claim 6 wherein $R^4$ and $R^5$ are hydrogen.

8. The method of claim 6 wherein the olefin is isobutylene.

9. The method of claim 1 wherein the crude reaction product of claim 1 comprises an amidoalkaiiesulfonic-acid represented by the formula

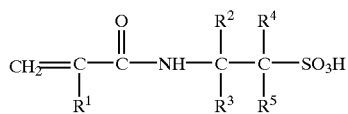

wherein each of $R^1$, $R^2$, $R^3$, $R^4$, and $R^5$, is independently hydrogen or an alkyl or hydrocarbyl radical containing up to about 7 carbon atoms and $R^2$ can further be $-CH_2SO_3H$, and mixtures of materials of the foregoing formula.

10. The method of claim 9 wherein said crude reaction product comprises mixtures of materials in which $R^3$ is $CH_3$ and in which $R^2$ is $CH_2SO_3H$.

11. The method of claim 9 wherein said crude reaction product further comprises isobutylenesulfollic acid.

12. The method of claim 9 wherein said crude reaction product further comprises t-butylacrylamide.

13. The method of claim 1 wherein the reaction product comprises 2-acrylamido-2-methylpropanesulfonic acid.

14. The method of claim 1 wherein the unsaturated nitrile is acrylonitrile, the source of $SO_3$ is oleum, and the olefin is isobutylene.

15. The method of claim 14 wherein the molar ratios of the materials supplied to the reaction are such that the ratio of oleum:isobutylene is about 0.8 to about 2 and the ratio of acrylonitrile:isobutylene is about 2 to about 20.

16. The method of claim 15 wherein the ratio of oleum:isobutylene is about 0.9 to about 1.5 and the ratio of acrylonitrile:isobutylene is about 5 to about 12.

17. The method of claim 1 wherein the crude reaction product from (a) contains unreacted unsaturated nitrice.

18. The method of claim 1 wherein the substantially non-aqueous medium is acrylonitrile.

19. The method of claim 1 wherein the reaction of step (a) is conducted at about −20° C. to about 40° C.

20. The method of claim 1 wherein step (a) comprises a first substep (i) of combining the unsaturated nitrile, the source of $SO_3$ and of the elements of water, and a second substep (ii) of adding the olefin to the mixture of (i).

21. The method of claim 20 wherein substep (i) is conducted at about −30 to about 0° C. and substep (ii) is conducted at about 20 to about 70° C.

22. The method of claim 1 wherein after step (a) the crude reaction mixture is neutralized.

* * * * *